United States Patent [19]
Wallace et al.

[11] Patent Number: 6,090,448
[45] Date of Patent: Jul. 18, 2000

[54] POLYOL-BASED PRECURSORS FOR PRODUCING NANOPOROUS SILICA THIN FILMS

[75] Inventors: Stephen Wallace, Albuquerque, N. Mex.; James Drage, Fremont, Calif.; Teresa Ramos; Douglas M. Smith, both of Albuquerque, N. Mex.

[73] Assignee: AlliedSignal Inc., Morristown, N.J.

[21] Appl. No.: 09/111,082

[22] Filed: Jul. 7, 1998

Related U.S. Application Data

[60] Provisional application No. 60/063,816, Oct. 31, 1997.
[51] Int. Cl.⁷ ...................................................... B05D 3/04
[52] U.S. Cl. ............... 427/337; 106/287.12; 106/287.14; 106/287.16; 427/255.4; 427/397.7
[58] Field of Search .................. 106/287.12, 287.14, 106/287.16; 427/397.7, 255.4, 337; 428/447, 446

[56] References Cited

FOREIGN PATENT DOCUMENTS

| 0459003 | 12/1991 | European Pat. Off. . |
|---|---|---|
| 0775669 | 5/1997 | European Pat. Off. . |
| 0776925 A2 | 6/1997 | European Pat. Off. . |

*Primary Examiner*—D. S. Nakarani
*Attorney, Agent, or Firm*—Leslie A. Weise

[57] ABSTRACT

The invention relates to nanoporous dielectric films and to a process for their manufacture. Such films are useful in the production of integrated circuits. Such films are produced from a precursor of an alkoxysilane; a relatively low volatility solvent composition comprising an ether of a $C_1$ to $C_4$ alkylene glycol which is miscible in water and alkoxysilanes, having a hydroxyl concentration of 0.021 mole/cm³ or less, a boiling point of about 175 ° C. or more at atmospheric pressure and a weight average molecular weight of about 100 or more; a relatively high volatility solvent composition having a boiling point below that of the relatively low volatility solvent composition; optional water and an optional catalytic amount of an acid.

29 Claims, 3 Drawing Sheets

POLYOL-BASED PRECURSORS FOR PRODUCING NANOPOROUS SILICA THIN FILMS

CROSS REFERENCE TO RELATED APPLICATION

This application claims the benefit of provisional application 60/063,816 filed Oct. 31, 1997 which is incorporated herein by reference.

BACKGROUND OF THE INVENTION

1. Field of the Invention

The present invention relates to nanoporous dielectric films and to a process for their manufacture. Such films are useful in the production of integrated circuits.

2. Description of the Prior Art

As feature sizes in the production of integrated circuits approach 0.25 μm and below, problems with interconnect RC delay, power consumption and crosstalk all become more significant. Integration of low dielectric constant (K) materials for interlevel dielectric (ILD) and intermetal dielectric (IMD) applications partially mitigate these problems however, each of the material candidates having K significantly lower than dense silica suffer from disadvantages. A number of organic and inorganic polymers have K in the range of 2.2 to 3.5, however, these polymers suffer from problems including low thermal stability, poor mechanical properties including low glass transition temperature (Tg), sample outgassing, and long term reliability questions. One alternative is to employ nanoporous silicas which can have dielectric constants in the range of about 1 to 3. Nanoporous silica is attractive because it employs similar precursors (e.g., TEOS, tetraethoxysilane) as used for spin-on glasses (SOG's) and CVD $SiO_2$ and because of the ability to control pore size of the nanoporous silica. In addition to low dielectric constant, nanoporous silica offers other advantages for microelectronics including thermal stability up to 900° C., small pore size (<< microelectronics features), use of materials that are widely used in the semiconductor industry, namely silica and precursors (e.g., TEOS), the ability to tune dielectric constant over a wide range, and deposition using similar tools as employed for conventional SOG processing.

Nanoporous silica films can be fabricated by using a mixture of a solvent composition and a silica precursor which is deposited onto a wafer by conventional methods of spincoating, dip-coating, etc. The silica precursor is polymerized by chemical and/or thermal means until it forms a gel. Film thickness and density/dielectric constant can be controlled independently by using a mixture of two solvents with significantly different volatility. The more volatile solvent evaporates during and immediately after precursor deposition. The second solvent is then removed by increasing the temperature. EP patent application EP 0 775 669 A2, which is incorporated herein by reference, shows a method for producing a nanoporous silica film with uniform density throughout the film thickness.

Nanoporous silicas are preferably prepared from precursors comprising an alkoxysilane, a relatively high volatility solvent and a relatively low volatility solvent which is a polyol having an ether linkage. The principal reactions for an alkoxysilane such as tetraethoxysilane, tetramethoxysilane, triethoxysilane, methyltriethoxysilane, colloidal silica, and silica precursors which contain silicon-organic-silicon linkages are shown below. The following are exemplary reactions since the extent of hydrolysis and transesterification can vary from 0 to 4.

1) Hydrolysis: $Si(OR)_4 + H_2O \longleftrightarrow Si(OR)_3OH + ROH$
2) Transesterification: $Si(OR)_4 + R"OH \longleftrightarrow Si(OR)_3OR" + ROH$
3) Water condensation: $Si(OR)_3OH + Si(OR)_3OH \longleftrightarrow Si(OR)_3OSi(OR)_3 + H_2O$
4) Alcohol condensation: $Si(OR)_3OH + Si(OR)_4 \longleftrightarrow Si(OR)_3OSi(OR)_3 + ROH$ Usually, an alcohol is used as the solvent which is the same as the alkoxy group on the silane. When polyols such as ethylene glycol or glycerol are employed, the situation is more complex. For a typical polyol, HOR'OH, transesterification can occur as:

5) Polyol transesterification: $Si(OR)_4 + HOR'OH \longleftrightarrow Si(OR)_3OR'OH + ROH$ The extent of transesterification depends upon the relative concentrations of water, alcohol and polyol as well as the reactivity of both the alcohol and polyol. The product of the right side of equation 5 can undergo additional water or alcohol reactions which yield a SiOR'OSi linkage as shown in equation 6.

6) Polyol condensation: $Si(OR)_3OR'OH + Si(OR)_3OH \longleftrightarrow Si(OR)_3OR'OSi(OR)_3 + H_2O$ Without the polyol, polymerization can occur only through SiOSi linkages but with the polyols, additional reaction pathways are created. The extent of modification that the polyol will have on the nanoporous silica evolution depends upon a number of factors which cannot be anticipated. It has now been found that the low volatility polyol solvent must meet a number of criteria which were previously not known in order to achieve a stable precursor solution. In addition to having a high boiling point and proper solubility in water and alkoxysilanes, important criteria are low hydroxyl concentration and high molecular weight.

An important criteria for obtaining polyol-based precursor solutions which are stable over long time (i.e. months) and which will give nanoporous silica films with desirable properties such as high surface area, high mechanical strength, and small pore size, is that solvents be employed with volumetric hydroxyl concentrations in the correct range. If the concentration is too high, reactions 5 and 6 will proceed to excess and the precursor molecular weight will grow with time before deposition. If the concentration is too low, the film will not exhibit desirable properties. The desired range of hydroxyl concentration depends on the target dielectric constant. The vapor pressure, and hence drying rate, of a fluid within a pore is different than for the pure fluid. This reduction in vapor pressure is a result of curvature of the liquid meniscus at the vapor-liquid interface. As the molecular weight increases, the reduction in vapor pressure increases and the drying rate decreases.

It has now been found that one group of low volatility solvents that is uniquely suited to meeting each of these constraints are the ethers of ethylene glycol and propylene glycol. The compounds useful for this invention have ether linkages (C—O—C) and are polyols (multiple alcohol groups on the same molecule). A single compound may be used or a mixture of compounds may be employed to achieve the desired properties.

SUMMARY OF THE INVENTION

The invention provides a nanoporous silica precursor composition which comprises at least one alkoxysilane; at least one relatively low volatility solvent composition comprising an ether of a $C_1$ to $C_4$ alkylene glycol which is miscible in water and alkoxysilanes, having a hydroxyl concentratio n of 0.021 mole/cm$^3$ or less, a boiling point of about 175° C. or more at atmospheric pressure and a weight average molecular weight of about 100 or more; at least one relatively high volatility solvent composition having a boiling point below that of the relatively low volatility solvent composition; optional water and an optional catalytic amount of an acid.

The invention further provides a process for forming a nanoporous dielectric coating on a substrate which comprises a) blending a nanoporous silica precursor composition comprising at least one alkoxysilane; at least one relatively low volatility solvent composition comprising an ether of a $C_1$ to $C_4$ alkylene glycol which is miscible in water and alkoxysilanes, having a hydroxyl concentration of 0.021 mole/cm$^3$ or less, a boiling point of about 175° C. or more at atmospheric pressure and a weight average molecular weight of about 100 or more; at least one relatively high volatility solvent composition having a boiling point below that of the relatively low volatility solvent composition; optional water and an optional catalytic amount of an acid, thus forming a mixture and causing a partial hydrolysis and partial condensation of the alkoxysilane;

b) depositing the composition onto a substrate while evaporating at least a portion of the relatively high volatility solvent composition;

c) exposing the composition to a water vapor and a base vapor; and d) evaporating the relatively low volatility solvent composition, thereby forming a relatively high porosity, low dielectric constant, silicon containing polymer composition on the substrate.

The invention also provides a semiconductor device produced by a process which comprises:

a) blending a nanoporous silica precursor composition comprising at least one alkoxysilane; at least one relatively low volatility solvent composition comprising an ether of a $C_1$ to $C_4$ alkylene glycol which is miscible in water and alkoxysilanes, having a hydroxyl concentration of 0.021 mole/cm$^3$ or less, a boiling point of about 175° C. or more at atmospheric pressure and a weight average molecular weight of about 100 or more; at least one relatively high volatility solvent composition having a boiling point below that of the relatively low volatility solvent composition; optional water and an optional catalytic amount of an acid, thus forming a mixture and causing a partial hydrolysis and partial condensation of the alkoxysilane;

b) depositing the composition onto a semiconductor substrate while evaporating at least a portion of the relatively high volatility solvent composition;

c) exposing the composition to a water vapor and a base vapor; and d) evaporating the relatively low volatility solvent composition, thereby forming a relatively high porosity, low dielectric constant, silicon containing polymer composition on the substrate.

It has now been found that by the use of the above ether of a $C_1$ to $C_4$ alkylene glycol in the precursor composition, that an unexpectedly stable precursor composition can be formed.

DETAILED DESCRIPTION OF THE PREFERRED EMBODIMENT

The invention forms a blend of at least one alkoxysilane with a relatively high volatility solvent composition, a relatively low volatility solvent composition, optional water and an optional catalytic amount of an acid. Water is included to provide a medium for hydrolyzing the alkoxysilane. This blend is then applied onto a substrate. The high volatility solvent evaporates during and immediately after deposition of the mixture. The low volatility solvent is then removed by increasing the temperature.

Useful alkoxysilanes for this invention include those which have the formula:

wherein at least 2 of the R groups are independently $C_1$ to $C_4$ alkoxy groups and the balance, if any, are independently selected from the group consisting of hydrogen, alkyl, phenyl, halogen, substituted phenyl. For purposes of this invention, the term alkoxy includes any other organic group which can be readily cleaved from silicon at temperatures near room temperature by hydrolysis. R groups can be ethylene glycoxy or propylene glycoxy or the like, but preferably all four R groups are methoxy, ethoxy, propoxy or butoxy. The most preferred alkoxysilanes nonexclusively include tetraethoxysilane (TEOS) and tetramethoxysilane.

The relatively high volatility solvent composition is one which evaporates at a temperature below, and preferably significantly below that of the relatively low volatility solvent composition. The relatively high volatility solvent composition preferably has a boiling point of about 120° C. or less, more preferably about 100° C. or less. Suitable high volatility solvent composition nonexclusively include methanol, ethanol, n-propanol, isopropanol, n-butanol and mixtures thereof. Other relatively high volatility solvent compositions which are compatible with the other ingredients can be readily determined by those skilled in the art.

The relatively low volatility solvent composition is one which evaporates at a temperature above, preferably significantly above that of the relatively high volatility solvent composition. The relatively low volatility solvent composition preferably has a boiling point of about 175° C. or more, more preferably about 200° C. or more. Suitable low volatility solvent compositions nonexclusively include an ether of a $C_1$ to $C_4$ alkylene glycol which is miscible in water and alkoxysilanes, having a hydroxyl concentration of 0.021 mole/cm$^3$ or less, with a boiling point of about 175° C. or more at atmospheric pressure and a weight average molecular weight of about 100 or more. Preferred low volatility solvent composition components include di(ethylene)glycol, tri(ethylene)glycol, tetra(ethylene)glycol; penta(ethylene) glycol, di(propylene)glycol, hexa(ethylene)glycol and mixtures thereof Their properties are as follows:

| Compound | Formula | Boiling Point °C. | Molecular Weight | Hydroxyl Concentration (mole/cm³) |
|---|---|---|---|---|
| di(ethylene)glycol | H(OCH₂CH₂)₂OH | 245 | 106.1 | 0.021 |
| tri(ethylene)glycol | H(OCH₂CH₂)₃OH | 285 | 150.17 | 0.015 |
| tetra(ethylene)glycol | H(OCH₂CH₂)₄OH | 314 | 194.2 | 0.012 |
| penta(ethylene)glycol | H(OCH₂CH₂)₅OH | 340 | 238.3 | 0.0095 |
| di(propylene)glycol | H(OCH₂H₂CH₂)₂OH | 231 | 134.2 | 0.0152 |
| hexa(ethylene)glycol | H(OCH₂CH₂)₆OH | 370 | 282.3 | 0.0080 |

It has further been found that the high and low volatility solvent compositions as well as the alkoxysilane should be ultrapurified prior to blending them together. When they are ultrapurified it has been found that the amount of trace metals in the resulting nanoporous layer is significantly reduced. This results in a reduction of layer interference such as RC delay, power consumption and crosstalk in the integrated circuits produced with these materials.

Within the context of the present invention, the term ultrapurified means that the solvent compositions should have no more than than about 250 parts per billion of trace metal impurities, preferably no more than about 50 parts per billion and more preferably no more than about 10 parts per billion of trace metal impurities. Such may be obtained by any convenient means such as by filtration, distillation or vacuum distillation.

The optional acid serves to catalyze the reaction of the alkoxysilane with the relatively high volatility solvent composition, a relatively low volatility solvent composition and water. Suitable acids are nitric acid and compatible organic acids which are volatile, i.e. which evaporate from the resulting reaction product under the process operating conditions, and which do not introduce impurities into the reaction product.

The alkoxysilane component is present in an amount of from about 3% to about 50% by weight of the overall blend. A more preferred range is from about 5% to about 45% and most preferably from about 10% to about 40%.

The high volatility solvent composition component is present in an amount of from about 20% to about 90% by weight of the overall blend. A more preferred range is from about 30% to about 70% and most preferably from about 40% to about 60%.

The low volatility solvent composition component is present in an amount of from about 1 to about 40% by weight of the overall blend. A more preferred range is from about 3% to about 30% and most preferably from about 5% to about 20%.

The mole ratio of water to silane is preferably from about 0 to about 50. A more preferred range is from about 0.1 to about 10 and most preferably from about 0.5 to about 1.5. The acid is present in a catalytic amount which can be readily determined by those skilled in the art. Preferably the molar ratio of acid to silane ranges from about 0 to about 0.2, more preferably from about 0.001 to about 0.05, and most preferably from about 0.005 to about 0.02.

The alkoxysilane containing composition is then coated on a substrate optionally having a pattern of lines on its surface, and forms a dielectric film on the surface. Typical substrates are those suitable to be processed into an integrated circuit or other microelectronic device. Suitable substrates for the present invention non-exclusively include semiconductor materials such as gallium arsenide (GaAs), silicon and compositions containing silicon such as crystalline silicon, polysilicon, amorphous silicon, epitaxial silicon, and silicon dioxide (SiO₂) and mixtures thereof. The layer is relatively uniformly applied to the substrate. The lines, when present, are lithographically formed and may be composed of a metal, an oxide, a nitride or an oxynitride. Suitable materials include silica, silicon nitride, titanium nitride, tantalum nitride, aluminum, aluminum alloys, copper, copper alloys, tantalum, tungsten and silicon oxynitride. These lines form the conductors or insulators of an integrated circuit. Such are typically closely separated from one another at distances of about 20 micrometers or less, preferably 1 micrometer or less, and more preferably from about 0.05 to about 1 micrometer.

After deposition, the high volatility solvent is then partially evaporated over a period of seconds or minutes. At this point, the film is a viscous liquid of the silica precursors and the less volatile solvent. Slightly elevated temperatures may optionally be employed to accelerate this step. Such temperatures may range from about 20° C. to about 80° C., preferably range from about 20° C. to about 50° C. and more range from about 20° C. to about 35° C.

Then the coating is exposed to both a water vapor and a base vapor. The base vapor may be introduced first followed by the water vapor, or both the water vapor and the base vapor may be introduced simultaneously. Water can be provided by ambient air containing moisture. The water vapor causes a continued hydrolysis of the alkoxysilane alkoxy groups, and the base catalyzes condensation of the hydrolyzed alkoxysilane and serves to increase molecular weight until the coating gels and ultimately increases gel strength.

If the condensation rate is much faster than hydrolysis, a significant number of alkoxy groups will remain after the gel point. If little hydrolysis has occurred, then the film will maintain the same thickness as after the coating step. Continued exposure to basic water vapor results in continued hydrolysis of alkoxy groups forming silanols and the generation of volatile alcohols. The film is then dried in a conventional way by solvent evaporation of the less volatile solvent with no further shrinkage. Elevated temperatures may be employed to dry the coating in this step. Such temperatures may range from about 20° C. to about 450° C., preferably from about 50° C. to about 350° C. and more preferably from about 175° C. to about 320° C. The silicon containing polymer composition preferably has a dielectric constant of from about 1.3 to about 3.5, more preferably from about 1.5 to about 3.0, and most preferably from about 1.8 to about 2.5. The pore size of silica composition ranges from about 1 nm to about 100 nm, more preferably from about 2 nm to about 30 nm, and most preferably from about 3 nm to about 20 nm. The density of the silicon containing composition, including the pores, ranges from about 0.25 to about 1.9 g/cm³, more preferably from about 0.4 to about 1.6 g/cm³, and most preferably from about 0.7 to about 1.2 g/cm³.

Suitable bases for use in the base vapor nonexclusively include ammonia and amines, such as primary, secondary and tertiary alkyl amines, aryl amines, alcohol amines and mixtures thereof which have a boiling point of about 200° C. or less, preferably 100° C. or less and more preferably 25° C. or less. Preferred amines are methyl amine, dimethyl amine, trimethyl amine, n-butyl amine, n-propyl amine, tetramethyl ammonium hydroxide, piperidine and 2-methoxyethyl amine. The ability of an amine to accept a proton in water is measured in terms of the basicity constant $K_b$, and $pK_b = \log K_b$. In the preferred embodiment, the $pK_b$ of the base may range from about less than 0 to about 9. A more preferred range is from about 2 to about 6 and most preferably from about 4 to about 5.

In the preferred embodiment, the mole ratio of water vapor to base vapor ranges from about 1:3 to about 1:100, preferably from about 1:5 to about 1:50, and more preferably from about 1:10 to about 1:30.

The following non-limiting examples serve to illustrate the invention.

EXAMPLE 1 (COMPARATIVE)

This example illustrates that an ethylene glycol based precursor has an unstable shelf-life when diluted with ethanol (EtOH). During synthesis, ethylene glycol undergoes a large amount of crosslinking in the polymer and the molecular weight grows. When the precursor is diluted to achieve the correct solids content for adequate deposition, the polymer immediately de-polymerizes making it unstable and unsuitable as a precursor.

A precursor was synthesized by adding 61.0 mL of tetraethoxysilane, 61.0 mL of ethylene glycol, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, it was stored in refrigeration at 4° C.

Figure 1:
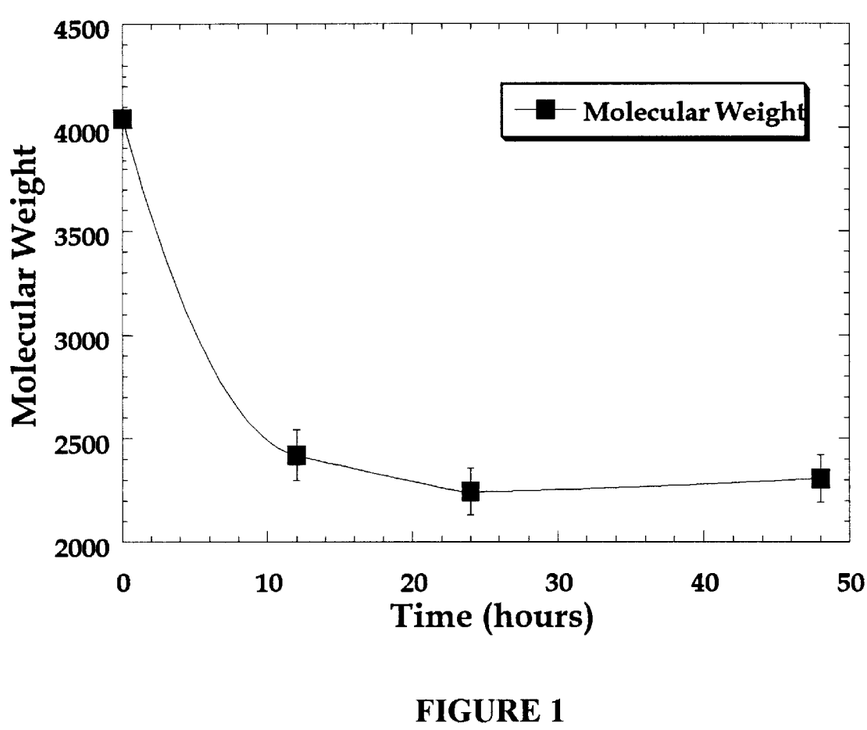
FIG. 1 is a graph of the change in molecular weight as a function of time for a ethanol-diluted ethylene glycol precursor.

Molecular weight measurements were performed to track the stability of the precursor by gel permeation chromatography (GPC) after the solution was diluted with ethanol to a 60% by weight amount. The solution is filtered to 0.2 $\mu$m with a teflon filter and diluted with tetrahydrofuran to a 0.15:1 (solution/tetrahydrofuran) volume ratio. Multiple samples (3) were run to confirm the reproducibility of the instrument. The average molecular weight was plotted as a function of time (in hours) as seen in FIG. 1 and Table 1. Within twelve hours upon ethanol dilution of the precursor, the molecular weight drops by 50% demonstrating that that the polymer is de-polymerizing.

TABLE 1

Change in molecular weight as a function of time for a ethanol-diluted ethylene glycol precursor.

| Time (hours) | Average Molecular weight |
|---|---|
| 0 | 4364 |
| 12 | 2419 |
| 24 | 2245 |
| 48 | 2307 |

EXAMPLE 2

This example illustrates that a tetraethylene glycol-based precursor has a more stable shelf-life when diluted with EtOH then the ethylene glycol-based precursor. Because the molecular weight of tetraethylene glycol is larger than ethylene glycol, the number of hydroxyls per volume is less in tetraethylene glycol, reducing the extent of crosslinking, and in-turn less de-polymerization occurs upon dilution.

The precursor was synthesized by adding 61.0 mL of tetraethoxysilane, 61.0 mL of tetraethylene glycol, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, it was stored in refrigeration at 4° C.

Figure 2:
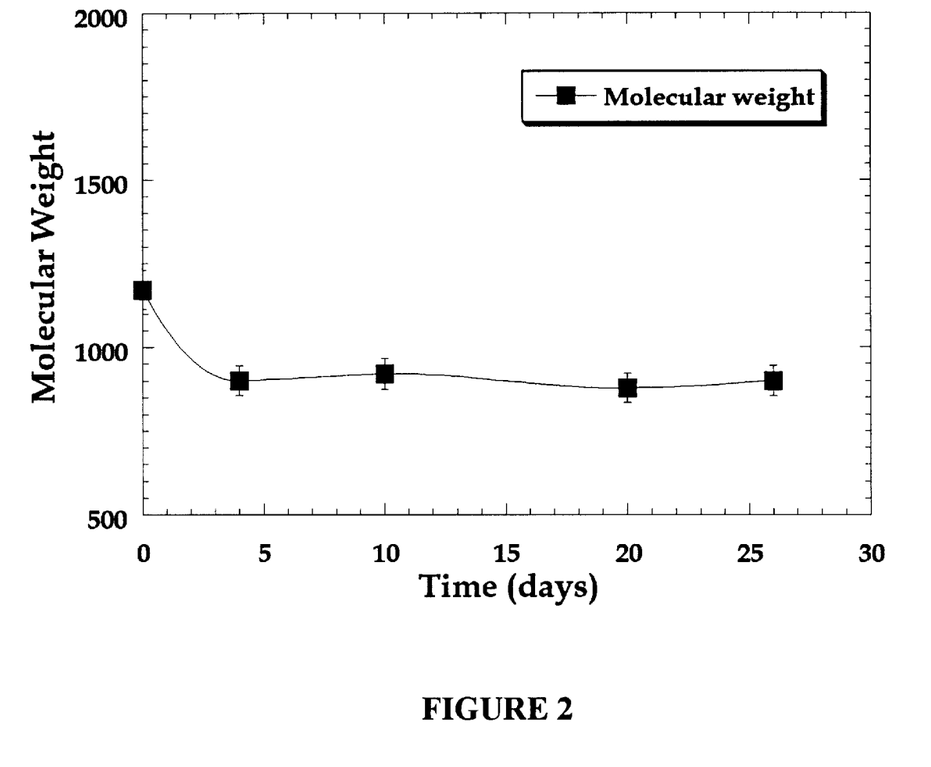
FIG. 2 is a graph of the change in molecular weight as a function of time for a ethanol diluted tetraethylene glycol precursor.

Molecular weight measurements were performed to track the stability of the precursor by gel permeation chromatography (GPC) after the solution was diluted with ethanol to a 50% by weight amount and 0.3% by weight with FC-430 surfactant (3M, St. Paul Minn. 55144). The solution is filtered to 0.2 $\mu$m with a teflon filter and diluted with tetrahydrofuran at a 0.15:1 (solution/tetrahydrofuran) volume ratio. Multiple samples (3) were run to confirm the reproducibility of the instrument. The average molecular weight was plotted as a function of time (in days) as seen in FIG. 2 and Table 2. The molecular weight drops by only 18% as compared to the ethylene glycol precursor as shown in Example 1 demonstrating that it is a more stable precursor.

TABLE 2

Change in molecular weight as a function of time for a ethanoldiluted tetraethylene glycol precursor.

| Time (hours) | Average Molecular weight |
|---|---|
| 0 | 1172 |
| 4 | 901 |
| 10 | 921 |
| 20 | 878 |
| 26 | 900 |

EXAMPLE 3 (COMPARATIVE)

This example illustrates that when ethylene glycol is diluted with ethanol, the solution is unstable and de-polymerizes. As a result, during the film formation process the film quality degrades very quickly with time.

The precursor was synthesized by adding 61.0 mL of tetraethoxysilane, 61.0 mL of ethylene glycol, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, the solution was diluted with ethanol to reduce the viscosity and achieve a desirable thickness. The diluted precursor was filtered to 0.1 $\mu$m using a teflon filter.

Approximately 2.0 ml of the precursor was deposited onto a 4 inch silicon wafer on a spin chuck, and spun on at 2500 rpm for 30 seconds. The films were aged for 10.0 minutes statically by adding 1 ml of 15M ammonium hydroxide to the bottom of a petri-dish. A film is placed on a stand in the petri-dish and the dish is covered. Water and ammonia from the base are evaporated in the dish and allowed to diffuse into the film to promote gelation and aging. The films were then solvent exchanged in a two step process by which ~20 mL of ethanol was spun on the film at 250 rpm for 10 seconds without allowing the film to dry. Approximately 20 nL of hexamethyldisilazane was immediately spun on the film at 250 rpm for 10 seconds. The films were heated at elevated temperatures for 1 min. each at 175° C. and 320° C. in air. Films were deposited and processed at different times after ethanol dilution as seen in Table 3.

TABLE 3

Thickness and refractive index of films diluted with ethanol for different times

| Time of dilution (hrs.) | Average thickness (Angstroms) | Refractive Index $n_f$ |
| --- | --- | --- |
| 0.5 | 7029 | 1.08 |
| 12 | film cracks during aging | film cracks during aging |
| 24 | film cracks during aging | film cracks during aging |
| 48 | film cracks during aging | film cracks during aging |

EXAMPLE 4

This example illustrates that good quality films can be made with tetraethylene glycol precursors because the precursor is more stable.

A precursor was synthesized by adding 61.0 mL of tetraethoxysilane, 61.0 mL of tetraethylene glycol, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, the solution was diluted with ethanol to reduce the viscosity and achieve a desirable thickness and 0.3% by weight with FC-430 surfactant (3M, St. Paul Minn. 55144). The diluted precursor was filtered to 0.1 µm using a teflon filter. Approximately 2.0 ml of the precursor was deposited onto a 4 inch silicon wafer on a spin chuck, and spun on at 2500 rpm for 30 seconds. The films were aged for 10.0 min. statically by adding 1 ml of 15M ammonium hydroxide to the bottom of a petri-dish. A film is placed on a stand in the petri-dish and the dish is covered. Water and ammonia from the base are evaporated in the dish and allowed to diffuse into the film to promote gelation and aging. The films were then solvent exchanged in a two step process by which ~20 mL of ethanol was spun on the film at 250 rpm for 10 seconds without allowing the film to dry. Approximately 20 mL of hexamethyldisilazane was immediately spun on the film at 250 rpm for 10 seconds.

The films were heated at elevated temperatures for 1 min. each at 175° C. and 320° C. in air. Films were deposited and processed at different times after ethanol dilution as seen in Table 4.

TABLE 4

Thickness and refractive index of films diluted with ethanol for different times

| Time of dilution (hrs.) | Average thickness (Angstroms) | Refractive Index $n_f$ |
| --- | --- | --- |
| 0.5 | 10450 | 1.09 |
| 4 | 10200 | 1.10 |
| 6 | 10300 | 1.095 |
| 11 | 10400 | 1.10 |

EXAMPLE 5

This example illustrates the different drying rates for ethylene glycol and tetraethylene glycol. Since the time required to process nanoporous silica thin films is on the order of minutes it is critical for the low volatility solvent to have minimal evaporation during the film formation process.

Figure 3:
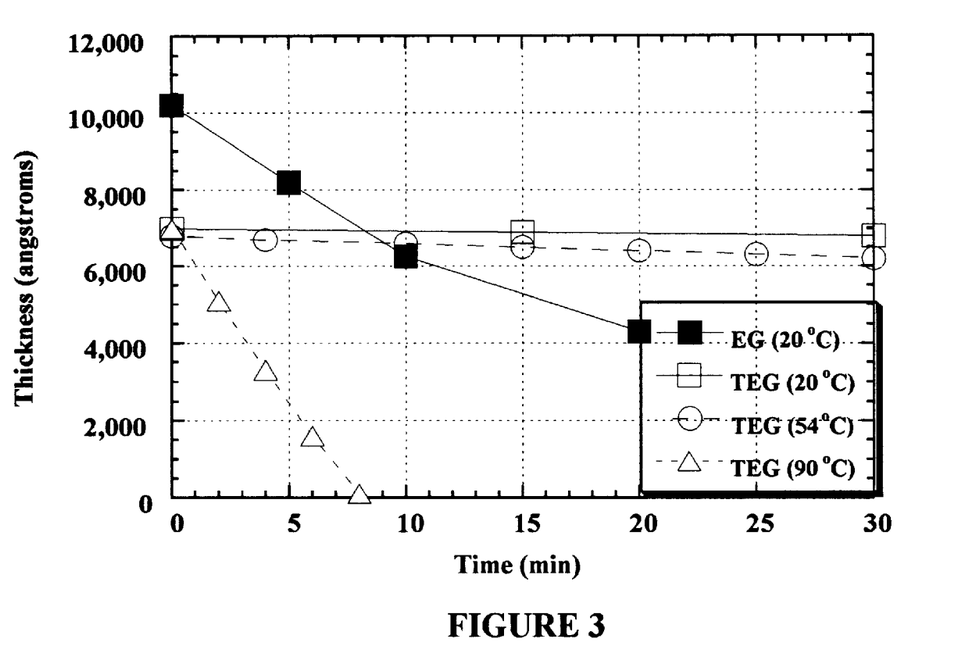
FIG. 3 is a graph of the drying rate of ethylene glycol and tetraethylene glycol films with no silica precursor as a function of time and temperature.

Ethylene glycol and tetraethylene glycol were diluted 60% and 50% by weight respectively with ethanol and mixed vigorously to mimic typical drying rates of nanoporous silica precursor solutions. Approximately 2 mls of the mixtures were deposited on a silicon substrate at 2500 rpm's for 30 seconds. The ethanol quickly evaporates during the spin and the low volatility glycol remains. The film thicknesses were measured as a function of time and temperature using ellipsometry. FIG. 3 illustrates the evaporation rates for the mixtures of ethylene glycol and tetraethylene glycol. As seen in FIG. 3 the rate of evaporation for ethylene glycol is quite high thus making it unsuitable for nanoporous silica processing, whereas the evaporation of tetraethylene glycol is quite low even at elevated temperatures.

EXAMPLE 6

This example demonstrates that distilling the precursor raw materials before synthesis of the nanoporous silica lowers the trace level metals content. It also allows a deposited and processed film to be low in metals when aerial density is measured by inductively coupled plasma mass spectrometry (ICP/MS) or graphite furnace atomic absorption spectroscopy (GFAAS).

The raw materials were distilled by one of two methods based on their boiling points and hydrolytic stability. EtOH was distilled by using a simple distillation apparatus. For all distillations, the first quarter of the total volume was distilled and discarded. The next one half of the total volume was distilled and collected. The EtOH was added to a flask and was heated to its boiling point. The distillation occurred by allowing the vapors to rise up a cooled condenser. After a few minutes the vapors became saturated and then condensed and were collected in a receiver flask. The collected solvent in a receiver flask was decanted and stored in a polypropylene bottle.

Tetraethoxysilane (TEOS) and tetraethylene glycol (TEG) were vacuum distilled due to TEOS being a readily hydrolyzable material and TEG having a high boiling point. The solvent was added to a two neck flask that was connected to a thermometer and a Friedrich condenser that was jacketed and flowing cooled water throughout it. The vacuum source was connected to the apparatus and the other end of the condenser was connected to the distillate flask. For distillation of TEOS, the sample was heated by connecting a variac to the heating mantle which was set at 30 volts. A vacuum of 15–20 torr was applied to the apparatus. TEOS vapors condensed and dripped into the distillate flask. This distillate of TEOS was then decanted into and stored in a polypropylene bottle at room temperature. For distillation of TEG, the variac was set to 40 volts and a vacuum of 15–20 torr was drawn on the apparatus. The solvent was purified and the distillate was decanted and stored in a polypropylene bottle at room temperature.

The precursor was synthesized by adding 61.0 mL of TEOS, 61.0 mL of TEG, 4.87 mL of deionized water, and 0.2 mL of 1N nitric acid together in a round bottom flask. The solution was allowed to mix vigorously then heated to ~80° C. and refluxed for 1.5 hours to form a solution. After the solution was allowed to cool, it was diluted 50% by weight with ethanol to reduce the viscosity and 0.3% by weight with FC-430 surfactant (3M St. Paul Minn. 55144). The diluted precursor was filtered to 0.1 µm using a teflon filter. A sample of the precursor was analyzed for trace metals. A second precursor was synthesized in the above matter, in which none of the raw materials were distilled for comparative purposes. The results are shown in Table 5 in parts per billion (ppb) units.

TABLE 5

Units in (ppb)

| Metal | Detection Limit (D.L.) | Precursor (raw materials not distilled) | Precursor (raw materials distilled) |
|---|---|---|---|
| Al | 0.05 | 0.42 | <0.05 |
| Sb | 0.05 | <0.05 | <0.05 |
| As | 0.1 | <0.1 | <0.1 |
| Ba | 0.01 | 0.014 | <0.01 |
| Be | 0.05 | <0.05 | <0.05 |
| Bi | 0.05 | <0.05 | <0.05 |
| Cd | 0.01 | <0.01 | <0.01 |
| Ca | 0.1 | 2.3 | 0.44 |
| Cr | 0.05 | <0.05 | <0.05 |
| Co | 0.01 | <0.01 | <0.01 |
| Cu | 0.05 | 0.49 | <0.05 |
| Ga | 0.01 | <0.01 | <0.01 |
| Ge | 0.05 | <0.05 | <0.05 |
| Fe | 0.1 | 0.44 | <0.1 |
| Pb | 0.05 | <0.05 | <0.05 |
| Li | 0.1 | 0.15 | <0.05 |
| Mg | 0.5 | 1.6 | 1.1 |
| Mn | 0.005 | <0.05 | <0.05 |
| Mo | 0.05 | <0.05 | <0.05 |
| Ni | 0.05 | <0.05 | <0.05 |
| K | 0.5 | 0.78 | 0.16 |
| Ag | 0.05 | <0.05 | <0.05 |
| Na | 0.5 | 4.3 | 1.2 |
| Sr | 0.005 | 0.012 | <0.01 |
| Sn | 0.1 | <0.05 | <0.05 |
| Ti | 0.2 | 1.1 | 0.43 |
| V | 0.05 | <0.1 | <0.1 |
| Zn | 0.1 | 1.4 | 0.45 |
| Zr | 0.005 | <0.05 | <0.05 |

In all cases the precursor in which the raw materials were distilled came out lower in trace metals than the non-distilled case.

Approximately 8–10 ml of the precursors were deposited onto 8 inch silicon wafers on a spin chuck, and spun at 2500 rpm for 30 seconds. The films were gelled and aged in a vacuum chamber using the following conditions: The chamber was evacuated to −20 inches of Hg. Next, 15M ammonium hydroxide was heated and equilibrated at 45° C. and dosed into the chamber to increase the pressure to −4.0 inches Hg for 2–3 minutes. Finally, the chamber was evacuated to −20.0 inches of Hg and backfilled with nitrogen. The film was heated at elevated temperatures for 1 min. each at 175° C. and 320° C. in air.

Films were analyzed for trace metal analysis. Metals were analyzed by either ICP-MS or GFAAS. A control was sent with the nanoporous films to determine the level of contamination on the substrate prior to film deposition. Table 6 shows the results of the metals analysis.

TABLE 6

(Units in E10 atoms/cm$^2$)

| Metal | Detection Limit (D.L.) | Control (blank no film) | Film 1 (raw materials not distilled) | Film 2 (raw materials distilled) |
|---|---|---|---|---|
| Al | 0.5 | <0.5 | 5.8 | 2.7 |
| Sb | 0.005 | <0.005 | 0.017 | <0.005 |
| As | 0.05 | <0.05 | <0.05 | <0.05 |
| Ba | 0.005 | 0.019 | 0.019 | 0.009 |
| Be | 0.5 | <0.5 | <0.5 | <0.5 |
| Bi | 0.002 | <0.002 | <0.002 | 0.080 |
| B | 1 | 120 | 711 | 192 |
| Cd | 0.01 | 0.03 | 0.03 | 0.04 |
| Ca | 0.5 | 1.6 | 21 | 9 |
| Cr | 0.1 | <0.1 | 0.3 | 1.5 |
| Co | 0.02 | <0.02 | <0.02 | <0.02 |
| Cu | 0.1 | 0.2 | 0.5 | 0.7 |
| Ga | 0.02 | <0.02 | 0.08 | 0.16 |
| Ge | 0.02 | <0.02 | <0.02 | <0.02 |
| Fe | 0.3 | <0.3 | 2.8 | 6.2 |
| Pb | 0.005 | 0.12 | 0.042 | 0.081 |
| Li | 0.1 | <0.1 | 0.1 | 0.2 |
| Mg | 0.5 | 1.2 | 7.8 | 2.6 |
| Mn | 0.005 | <0.005 | 0.096 | 0.15 |
| Mo | 0.05 | <0.05 | <0.05 | 0.09 |
| Ni | 0.05 | 1.2 | 0.47 | 0.85 |
| K | 0.5 | <0.5 | 15 | 8 |
| Ag | 0.05 | <0.05 | <0.05 | <0.05 |
| Na | 0.5 | 1.5 | 30 | 10 |
| Sr | 0.005 | <0.005 | 0.027 | 0.008 |
| Sn | 0.1 | 1.0 | 0.9 | 0.1 |
| Ti | 0.2 | <0.2 | 1.0 | 1.0 |
| V | 0.05 | <0.05 | 0.09 | <0.05 |
| Zn | 0.1 | 3.9 | 2.7 | 2.6 |
| Zr | 0.005 | <0.005 | 0.17 | 0.12 |

The results show that distilling the raw materials leads to a lower metal aerial density. Two metal levels, sodium and potassium, are quite critical for semiconductor processing. These metals were decreased by a factor of 2 to a very low level after distillation.. Boron was one metal that came out high but the control was found to have high amounts as well, due to having higher levels of boron dopant in the silicon substrates.

From the foregoing examples it can be seen that precursors prepared from $C_1$ to $C_4$ alkylene glycol ethers meeting the criteria of this invention have a more stable shelf-life than precursors prepared from alkylene glycols.

What is claimed is:

1. A nanoporous silica precursor composition which comprises at least one alkoxysilane; at least one relatively low volatility solvent composition comprising an ether of a $C_1$ to $C_4$ alkylene glycol which is miscible in water and alkoxysilanes, having a hydroxyl concentration of 0.021 mole/cm$^3$ or less, a boiling point of about 175° C. or more at atmospheric pressure and a weight average molecular weight of about 100 or more; at least one relatively high volatility solvent composition having a boiling point below that of the relatively low volatility solvent composition; optional water and an optional catalytic amount of an acid.

2. The composition of claim 1 which comprises water.

3. The composition of claim 1 which comprises a catalytic amount of an acid.

4. The composition of claim 1 which comprises both water and a catalytic amount of an acid.

5. The composition of claim 1 which is absent of water and absent of an acid catalyst.

6. The composition of claim 1 wherein the alkoxysilane comprises one or more components selected from the group consisting of alkoxysilanes having the formula:

wherein at least 2 of the R groups are independently $C_1$ to $C_4$ alkQxy groups and the balance, if any, are independently selected from the group consisting of hydrogen, alkyl, phenyl, and halogen.

7. The composition of claim 6 wherein each R is methoxy, ethoxy or propoxy.

8. The composition of claim 1 wherein the alkoxysilane comprises one or more components selected from the group consisting of tetraethoxysilane and tetramethoxysilane.

9. The composition of claim 1 wherein the relatively high volatility solvent composition has a boiling point of about 120° C. or less.

10. The composition of claim 1 wherein the relatively high volatility solvent composition comprises one or more components selected form the group consisting of methanol, ethanol, n-propanol, isopropanol, n-butanol and mixtures thereof.

11. The composition of claim 1 wherein the relatively low volatility solvent composition comprises di(ethylene)glycol, tri(ethylene)glycol, tetra(ethylene)glycol; penta(ethylene)glycol, di(propylene)glycol, hexa(ethylene)glycol or mixtures thereof.

12. The composition of claim 1 wherein the precursor composition has no more than about 250 parts per billion of trace metal impurities.

13. A process for forming a nanoporous dielectric coating on a substrate which comprises
  a) blending a nanoporous silica precursor composition comprising at least one alkoxysilane; at least one relatively low volatility solvent composition comprising an ether of a $C_1$ to $C_4$ alkylene glycol which is miscible in water and alkoxysilanes, having a hydroxyl concentration of 0.021 mole/cm³ or less, a boiling point of about 175° C. or more at atmospheric pressure and a weight average molecular weight of about 100 or more; at least one relatively high volatility solvent composition having a boiling point below that of the relatively low volatility solvent composition; optional water and an optional catalytic amount of an acid, thus forming a mixture and causing a partial hydrolysis and partial condensation of the alkoxysilane;
  b) depositing the composition onto a substrate while evaporating at least a portion of the relatively high volatility solvent composition;
  c) exposing the composition to a water vapor and a base vapor; and
  d) evaporating the relatively low volatility solvent composition, thereby forming a silicon containing polymer composition on the substrate, wherein the silicon containing polymer composition has a dielectric constant of from about 1.3 to about 3.5. and a density in the range of from about 0.25 to about 1.9 g/cm³.

14. The process of claim 13 wherein step (a) comprises blending water in the composition.

15. The process of claim 13 wherein step (a) further comprises blending a catalytic amount of an acid in the composition.

16. The process of claim 13 wherein the alkoxysilane comprises one or more components selected from the group consisting of alkoxysilanes having the formula:

wherein at least 2 of the R groups are independently $C_1$ to $C_4$ alkoxy groups and the balance, if any, are independently selected from the group consisting of hydrogen, allyl, phenyl, and halogen.

17. The process of claim 16 wherein each R is methoxy, ethoxy or propoxy.

18. The process of claim 13 wherein the alkoxysilane comprises one or more components selected from the group consisting of tetraethoxysilane and tetramethoxysilane.

19. The process of claim 13 wherein the relatively high volatility solvent composition has a boiling point of about 120° C. or less.

20. The process of claim 13 wherein the relatively high volatility solvent composition comprises one or more components selected form the group consisting of methanol, ethanol, n-propanol, isopropanol, n-butanol and mixtures thereof.

21. The process of claim 13 wherein the relatively low volatility solvent composition comprises di(ethylene)glycol, tri(ethylene)glycol, tetra(ethylene)glycol; penta(ethylene)glycol, di(propylene)glycol, hexa(ethylene)glycol or mixtures thereof.

22. The process of claim 13 wherein the base vapor comprises one or more components selected from the group consisting of ammonia, amines and mixtures thereof.

23. The process of claim 13 wherein the mole ratio of water vapor to base vapor ranges from about 1:3 to about 1:100.

24. The process of claim 13 wherein the base vapor has a pKb of from about less than 0 to about 9.

25. The process of claim 13 wherein the substrate comprises raised pattern of lines comprising a metal, silica, silicon nitride, titanium nitride, tantalum nitride or silicon oxynitride.

26. The process of claim 13 wherein the substrate comprises a semiconductor material.

27. The process of claim 13 wherein the substrate comprises silicon or gallium arsenide.

28. The process of claim 13 wherein the mole ratio of water vapor to base vapor ranges from about 1:3 to about 1:100.

29. The process of claim 13 wherein the precursor composition has no more than about 250 parts per billion of trace metal impurities.

* * * * *